(12) United States Patent
Warren

(10) Patent No.: US 9,681,991 B1
(45) Date of Patent: Jun. 20, 2017

(54) ADJUSTABLE PRESSURE LEG WRAP

(71) Applicant: Julie Warren, Pasadena, CA (US)

(72) Inventor: Julie Warren, Pasadena, CA (US)

( * ) Notice: Subject to any disclaimer, the term of this patent is extended or adjusted under 35 U.S.C. 154(b) by 0 days.

(21) Appl. No.: 14/756,201

(22) Filed: Aug. 17, 2015

(51) Int. Cl.
  *A61F 13/00* (2006.01)
  *A61F 13/08* (2006.01)

(52) U.S. Cl.
  CPC .. *A61F 13/00059* (2013.01); *A61F 13/00038* (2013.01); *A61F 13/00046* (2013.01); *A61F 13/08* (2013.01); *A61F 13/085* (2013.01)

(58) Field of Classification Search
  CPC ................................................. A61F 13/533
  See application file for complete search history.

(56) References Cited

U.S. PATENT DOCUMENTS

| | | | | |
|---|---|---|---|---|
| 2,854,000 | A | * | 9/1958 | Anderson ............. A61F 5/0585 602/36 |
| 2004/0249329 | A1 | * | 12/2004 | Hess ..................... A61F 5/0109 602/63 |
| 2010/0312160 | A1 | * | 12/2010 | Creighton ............... A61F 13/10 602/62 |
| 2011/0009795 | A1 | * | 1/2011 | Graham ................ A61F 13/085 602/75 |
| 2011/0125183 | A1 | * | 5/2011 | Lipshaw ............... A61F 13/085 606/201 |
| 2012/0179084 | A1 | * | 7/2012 | Lipshaw ............... A61F 13/085 602/75 |
| 2013/0319128 | A1 | * | 12/2013 | Richardson .............. G01N 3/08 73/818 |
| 2015/0025424 | A1 | * | 1/2015 | Richardson ........... A61F 13/085 601/84 |
| 2016/0030251 | A1 | * | 2/2016 | Schuren ................ A61F 5/0109 602/75 |

* cited by examiner

*Primary Examiner* — Tarla Patel
(74) *Attorney, Agent, or Firm* — William W. Haefliger

(57) ABSTRACT

A leg wrap to exert pressure on the lower leg, comprising lower leg sized fabric extending generally vertically to provide left and right tightenable sections, at least one of the sections carrying at least two vertically spaced straps extending generally horizontally and sidewardly of the other section, at least two straps configured to be adjustably connected to that other section in progressively wrap-tightening relation, about the lower leg, the sections consisting at least in part of elastically stretchable porous material allowing air passage through that material to ventilate wrapped portions of the lower leg. Strap compression indicating markers are also provided.

16 Claims, 6 Drawing Sheets

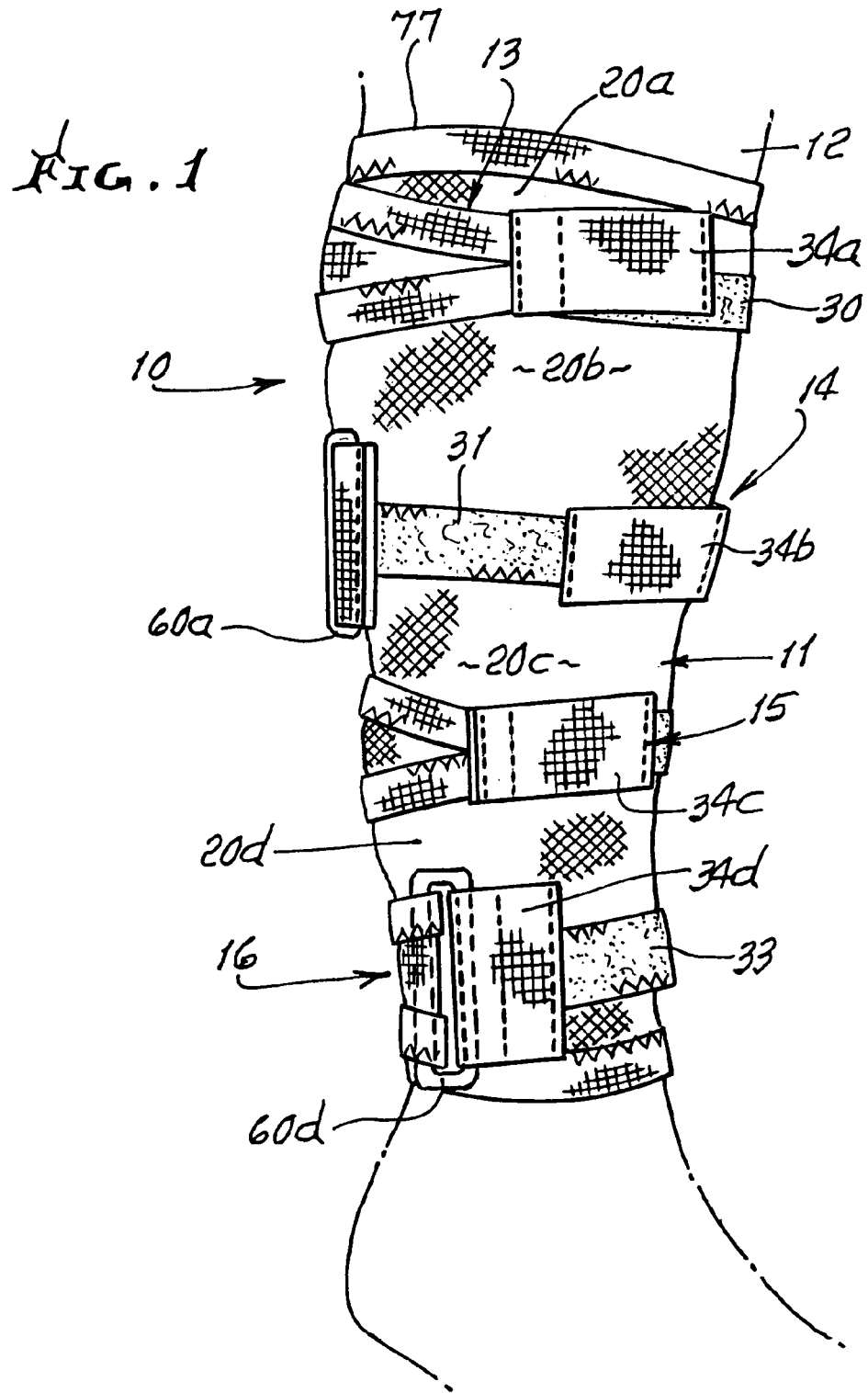

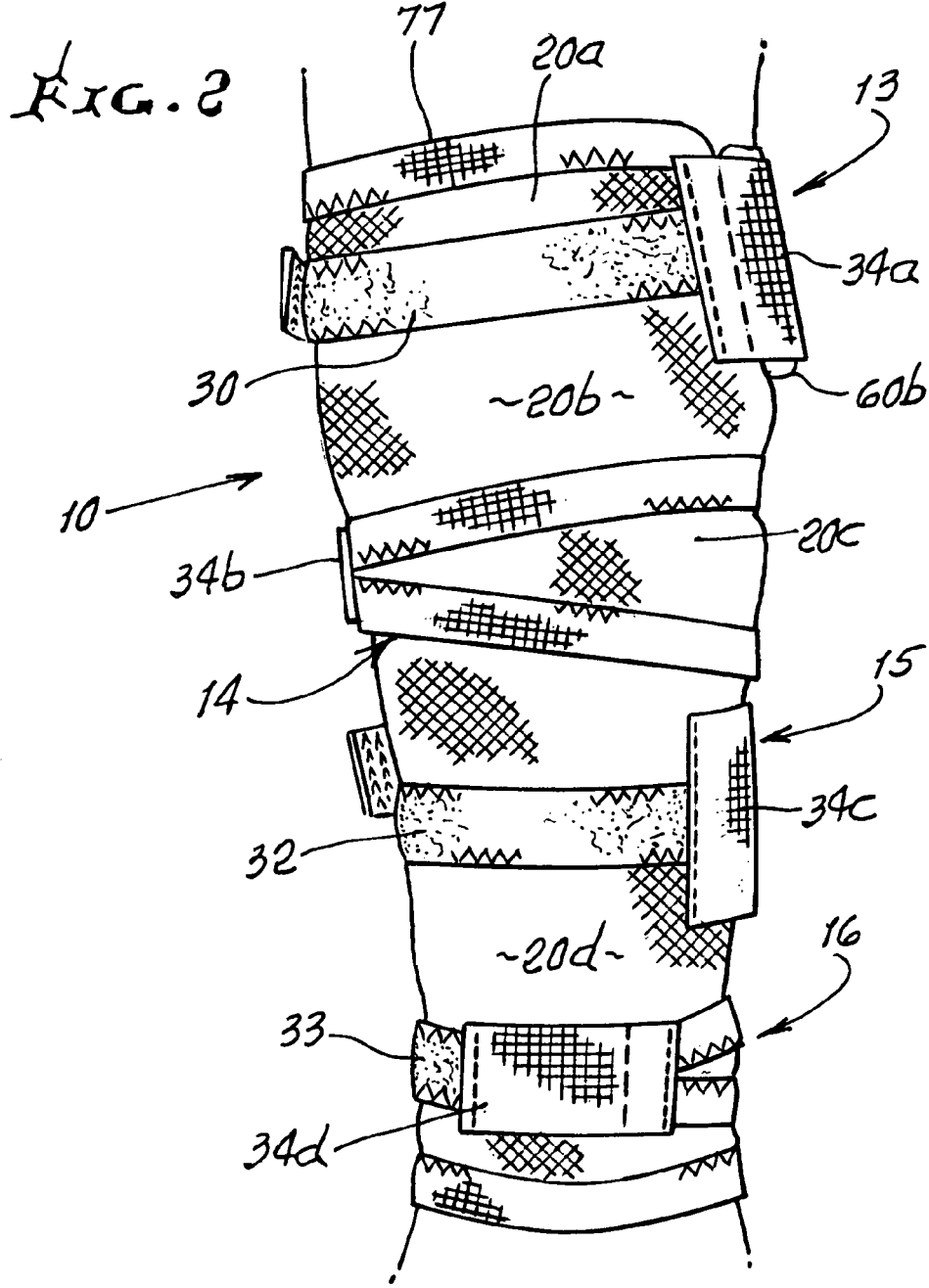

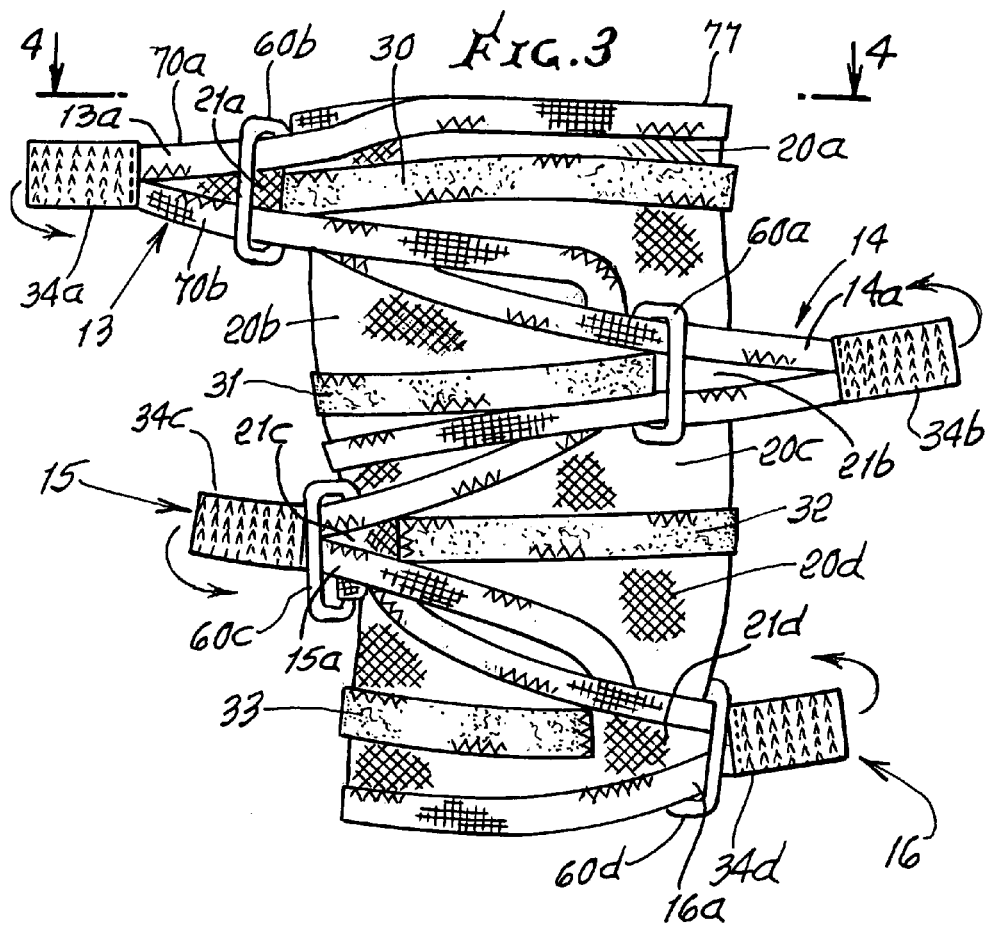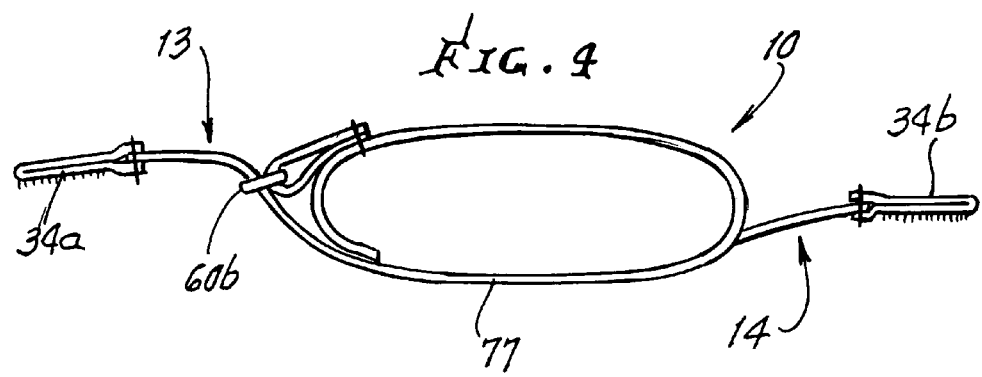

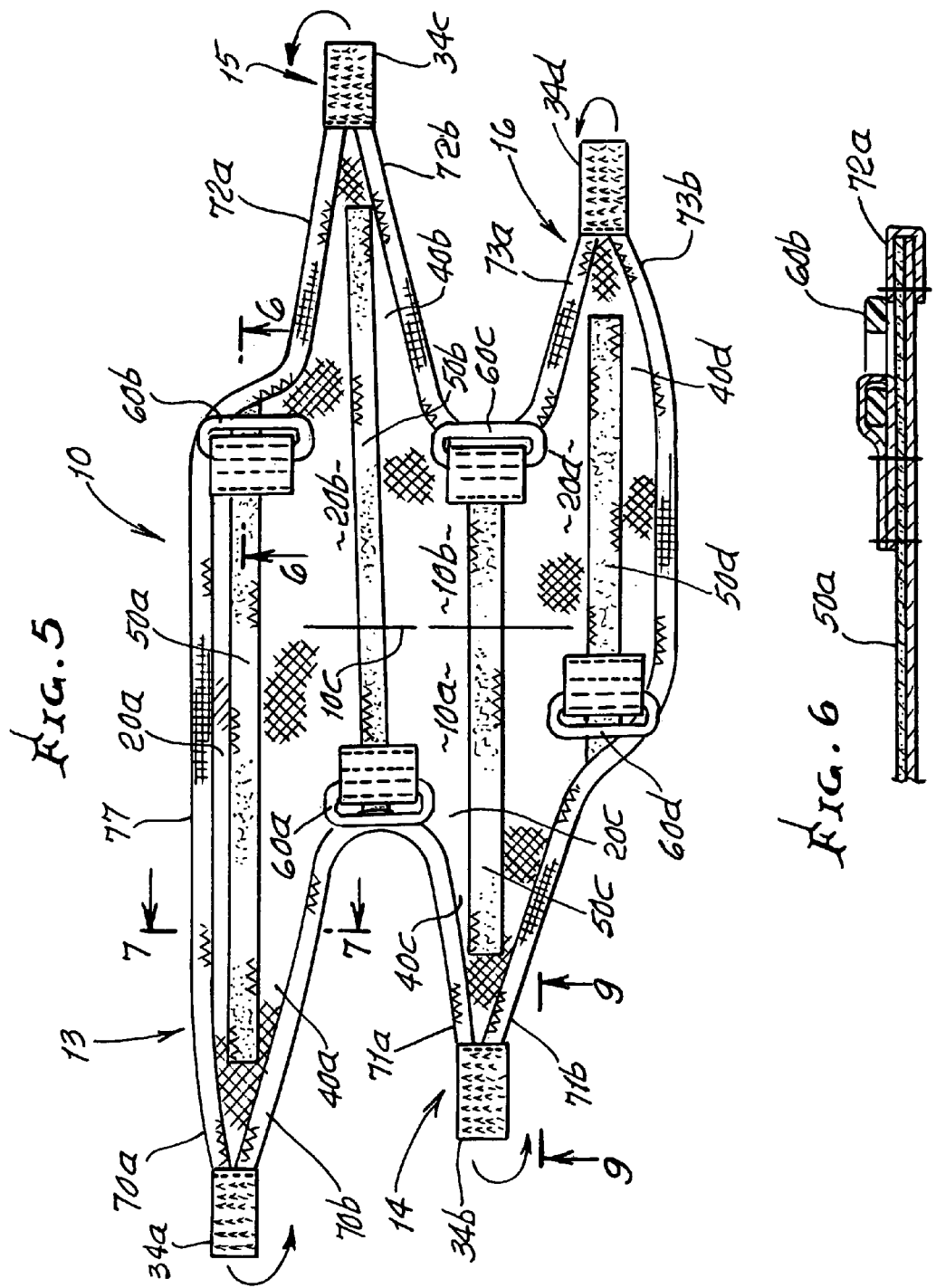

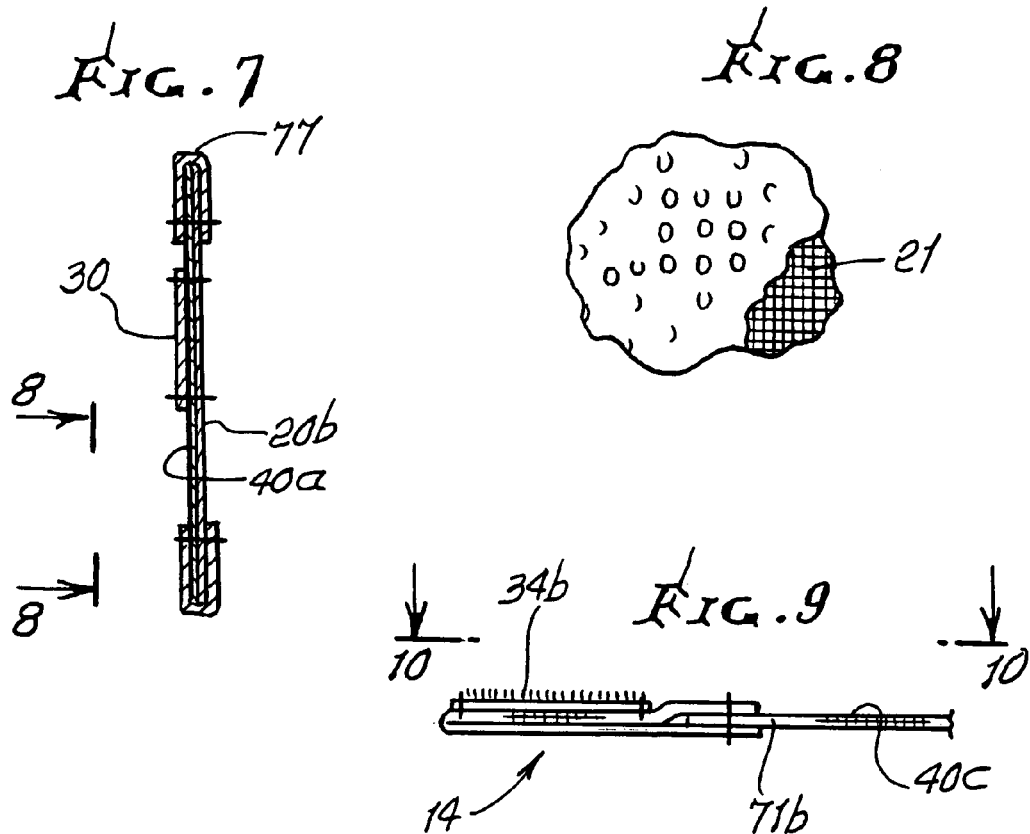
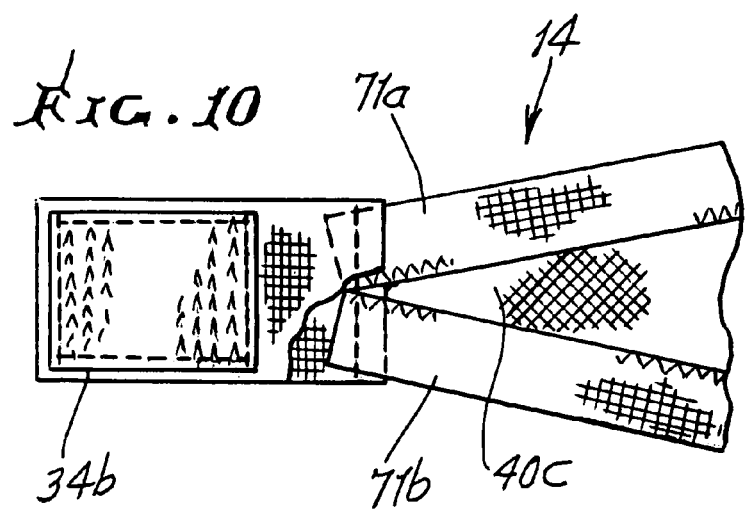

ADJUSTABLE PRESSURE LEG WRAP

BACKGROUND OF THE INVENTION

This invention relates generally to wrap apparatus configured to fit about the lower leg, i.e. below knee level, for therapeutic purposes; and more particularly concerns sturdy, easily applied, leg wrap apparatus tightenable at multiple locations to enable wrap adjustment at different locations on the lower leg.

There is need for easily applied and adjustable, lower leg wraps, which facilitate precise adjustment and selected force application to the lower leg, and which ventilate the lower leg and are comfortable to wear. There is also need for wraps having multiple straps which are individually adjustable, and meet the need for individual strap adjustment, which does not displace the wrap about the lower leg, during strap tightening adjustment.

SUMMARY OF THE INVENTION

It is a major object of the invention to provide an improved lower leg wrap construction meeting the above needs. Basically, the improved lower leg wrap comprises:

a) lower leg sized fabric extending generally vertically to provide left and right tightenable sections, b) at least one of said sections carrying at least two vertically spaced straps extending generally horizontally and sidewardly of the other section, said at least two straps configured to be adjustably connected to that other section in progressively wrap-tightening relation, about the lower leg, c) said sections consisting at least in part of porous material allowing air passage through that material to ventilate wrapped portions of the lower leg.

As will be seen, the leg wrap two straps extend in opposite direction, and at different elevations relative to said sections.

Another object concerns provision of four of said straps, two of which extend in one direction, and the other two of which extend in the opposite direction, relative to said sections. In this regard, the four straps typically extend generally horizontally, i.e. in substantially parallel relation, at different elevations and define first, second, third and fourth said straps, the first and third straps extending in one direction, and the second and fourth straps extending in the opposite direction.

Yet another object includes provision of wrap sections that have non-porous bands extending generally horizontally and which are spaced apart vertically, said porous material located vertically between said bands. In this regard, the straps typically taper generally horizontally from one section toward and over the other section, for accurate tightening force concentration, as during tightening.

Added objects include a wrap with indicia on at least one of said straps serving to indicate strap acceptable compression on the leg when the wrap is applied to the leg. Such a wrap includes indicia on multiple of said straps serving to indicate multiple acceptable compression levels on the leg when the wrap is applied to the leg and the strap is tensioned and affixed to said other section. Such a wrap typically includes indicia that include markers on the strap and on said other section positioned to visibly relatively approach one another as the strap is tensioned. Such a wrap may also include multiple pairs of markers, each pair including a first marker on a strap and second marker on the other section, and positioned to visibly relatively approach one another as the first marker approaches the second marker during strap tensioning.

Also, another object is to provide colored such markers, wherein the indicated pair of markers may have the same coloring, each pair indicating a degree of strap compression, preferable levels of compression indicated at 20, 30, and 40 mm Hg compression exertion on the leg.

These and other objects and advantages of the invention, as well as the details of an illustrative embodiment, will be more fully understood from the following specification and drawings, in which:

DRAWING DESCRIPTION

FIG. 1 is an external side elevation showing a wrap applied to the lower leg;

FIG. 2 is an internal side elevation view of the applied wrap;

FIG. 3 is a side elevation of the partially closed wrap itself;

FIG. 4 is a plan view taken on lines 4-4 of FIG. 3;

FIG. 5 is a plan view of the wrap itself in extended configuration;

FIG. 6 is an enlarged section taken on lines 6-6 of FIG. 5;

FIG. 7 is an enlarged section taken on lines 7-7 of FIG. 5;

FIG. 8 is fragmentary and enlarged side view section taken on lines 8-8 of FIG. 7;

FIG. 9 is an enlarged fragmentary edge view taken on lines 9-9 of FIG. 5;

FIG. 10 is a further enlarged view taken on lines 10-10 of FIG. 9.

DETAILED DESCRIPTION

Figure 11:
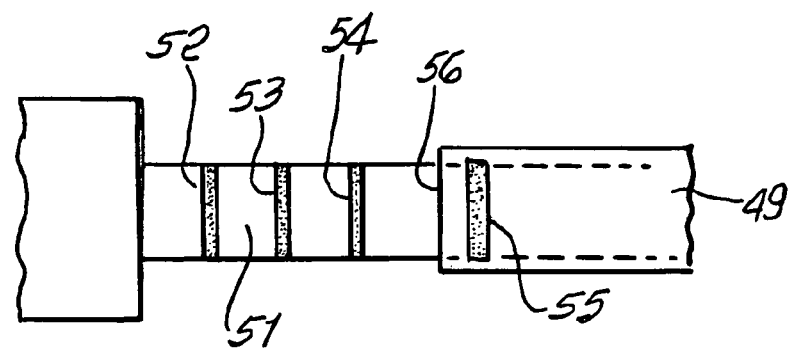
FIGS. 11 through 13 shows a modification.

Referring to FIGS. 1-3, basic elements of the wrap structure are shown to include:

a) lower leg sized fabric 11 of the wrap 10, extending generally vertically alongside the wearer's lower leg 12, to provide left and right tightenable wrap sections 10a and 10b merging at 10c, b) at least one of the sections, for example section 10a, carrying at least two vertically spaced straps, (for example two straps 13 and 14, four straps 13-16 being shown), and being preferable for best fit and ease of application, the straps extending lengthwise generally horizontally and sidewise of the other section 10b; the straps 13 and 14 of section 10c being configured to be adjustably wrap connected to the other section 10b in progressively wrap-tightening relation, about the lower leg, and the straps 15 and 16 configured to be wrap connected to section 10a, c) the sections 10a and 10b consisting, at least in part, of elastically stretchable, porous material (shown for example at 20a . . . 20d) and oriented to allow free flow air passage through porous fabric 21 to ventilate adjacent wrapped portions of the lower leg, for comfort of the skin closely underlying the wrap.

Additional features of the invention include the following:

i) inclusion of non-porous elastically stretchable bands extending generally horizontally and spaced apart vertically, said porous material located vertically between said bands, and stitch connected to the bands, lengthwise thereof and along band edges.

Such bands are shown at 30-33 in FIG. 3, and they extend generally horizontally mid-way widthwise of the porous fabric indicated at 21a . . . 21d extending toward fastenable end portions 34a . . . 34d of the straps. The straps taper as at 13a . . . 16a toward such end portions. Such tapering extends leftwardly at 13a and 15a, and rightwardly at 14a and 16a whereby tightening forces are balanced in directions about the lower leg, for enhanced comfort. Note that the straps 13a and 15a taper generally horizontally leftwardly, and the alternate straps 14a and 16a taper generally horizontally rightwardly. The wrap sections define edges 77 which have curvature indicated at 40a . . . 40d, in FIG. 5 between the straps.

FIG. 5 shows the provision of generally parallel force directing bands 50a . . . 50d extending on the porous fabric between the tapering end portions of the straps 13-16, and buckles 60a . . . 60d, the bands shown as connected to buckles.

Edges of the porous material carry strips in the form of seam binding 70a and 70b along edges of the tapering strap at 13; binding 71a and 71b along edges of the tapering strap at 14; 72a and 72b along edges of the tapering strap at 15; and 73a and 73b along edges of the tapering strap at 16.

Band ends 34a . . . 34d extend through the buckles to adjustably adhere to strap tubular end extents, upon tightening.

Figure 12:
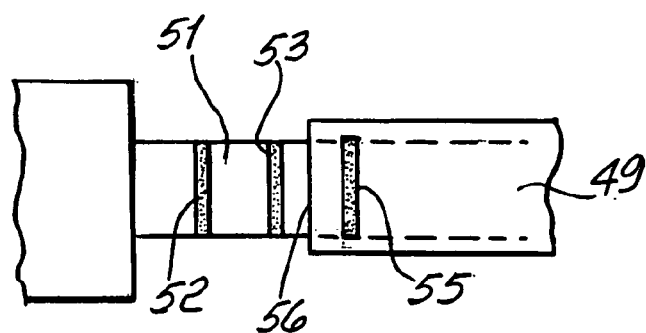
Figure 13:
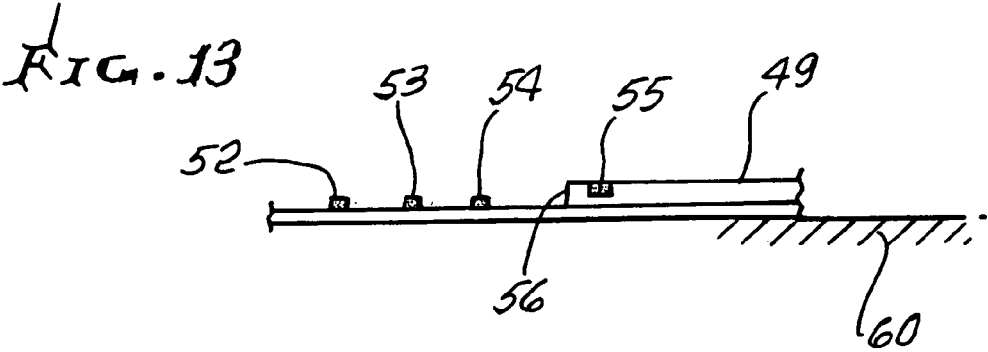

In FIGS. 11-13, linear indicia such as markers are shown on porous resiliently stretchable fabric material 51 (like material 21a) and at 52, 53 and 54 spaced locations. See also marker 55 on and near end 56 of the strap. When the strap is stretched, for example until marker 55 registers with marker 54, the user knows that a certain compression is being exerted on leg 60 by the wrap 57; and likewise, if the strap is further tensioned until marker 55 registers with marker 53, a known acceptable compression is being exerted by the wrap on the leg.

Accordingly, multiple pairs of markers are provided, each pair including a first marker on a strap and second marker on the other section and positioned to visibly relatively approach one another as the first marker approaches the second marker during strap tensioning.

The markers desirably have coloring indicating for example one of the following:
 i) about 20 mm Hg of strap compression on user's leg;
 ii) about 30 mm Hg of strap compression on user's leg;
 iii) about 40 mm Hg of strap compression on user's leg.

More desirably, these sequential markers are provided on the base material 51, and one marker 55 on the strap 49, near its end. When the strap is pulled to register marker 55 with marker 52 on the base material 51, the yieldable stretchability of the strap and base is such as to produce wrap compression $C_1$ on the leg, and when the strap is pulled to register marker 55 with marker 53 on base material 51, compression $C_2$ is exerted on the leg; and compression $C_3$ is exerted by the wrap when marker 55 is registered with marker 54 on the base material. The under surface local region of the strap adheres to the top surface region of the base material next to the markers when the two are pressed together, and those regions separate when the strap is pulled loose. Suitable adhesive is used on the strap and/or base.

Typical preferred compression levels are:
 C1=20 mm Hg (white marker)
 C2=30 mm Hg (red marker)
 C3=40 mm Hg (blue marker)

Markers may be yellow. Other colors may be used depending upon size of leg wrap.

What is claimed is:

1. A leg wrap to exert pressure on the lower leg, comprising
 a) lower leg sized fabric extending generally vertically to provide left and right tightenable fabric sections,
 b) at least one of said sections carrying at least two vertically spaced straps extending generally horizontally and sidewardly of another said section, said at least two straps configured to be adjustably connected to that other section in progressively wrap-tightening relation, about the lower leg, said straps configured as a pair of seam binding,
 c) said sections consisting at least in part of elastically stretchable porous material allowing air passage through that material to ventilate wrapped portions of the lower leg,
 d) there being multiple buckles engaging at least two pairs of said seam binding, each said seam binding pair tapering toward and engaging one of said buckles, the seam binding pairs that respectively taper toward alternate buckles being divergent therefrom in opposite directions,
 e) and wherein the wrap sections include non-porous elastically stretchable bands stitch connected to the porous material and extending generally horizontally and spaced apart vertically, said porous material located vertically between said bands, each said band being endwise connected to a buckle.

2. The leg wrap of claim 1 wherein said straps taper generally horizontally from one section away from and over the other section.

3. The leg wrap of claim 1 wherein said straps extend generally horizontally between and connected to said bands.

4. The leg wrap of claim 3 wherein said sections, define edges which have curvature between said straps.

5. The leg wrap of claim 1 wherein said sections define edges which have curvature between said straps.

6. The leg wrap of claim 1 wherein said two straps extend in opposite directions, and at different elevations relative to said sections.

7. The leg wrap of claim 1 wherein there are four of said straps two of which extend in one direction, and the other two of said four straps which extend in the opposite direction, relative to said sections.

8. The leg wrap of claim 1 wherein there are four of said straps which extend generally horizontally, at different successive elevations, and define first, second, third and fourth said straps, the first and third straps extending in one direction, and the second and fourth straps extending in the opposite direction.

9. The wrap of claim 1 including indicia on at least one of said straps serving to indicate strap acceptable compression on the leg when the wrap is applied to the leg.

10. The wrap of claim 9 including indicia on multiple of said markers serving to indicate multiple acceptable compression on the leg when the wrap is applied to the leg and the strap is tensioned and applied to said other section.

11. The wrap of claim 10 wherein said indicia includes multiple pairs of markers, each pair including a first marker on a strap and second marker on the other section and positioned to visibly relatively approach one another as the first marker approaches the second marker during strap tensioning.

12. The wrap of claim 11 wherein the pairs of multiple markers incorporate different colors.

13. The wrap of claim 12 wherein there are three indicia, and
 i) a first having a first color that indicates about 20 mm Hg of strap compression on user's leg;
 ii) a second having a second color that indicates about 30 mm Hg of strap compression on user's leg;
 iii) and a third having a third color that indicates about 40 mm Hg of strap compression on user's leg;
 additional colors could be used to indicate enlarged sizes.

14. The wrap of claim 9 wherein said indicia include markers on the strap and on said other section positioned to visibly relatively approach on another as the strap is tensioned.

15. The wrap of claim 14 wherein markers incorporate coloring.

16. The wrap of claim 15 wherein the coloring indicates one of the following:
   i) about 20 mm of strap compression on user's leg;
   ii) about 38 mm of strap compression on user's leg;
   iii) about 58 mm of strap compression on user's leg.

\* \* \* \* \*